United States Patent
Jeong et al.

(10) Patent No.: US 12,228,542 B2
(45) Date of Patent: Feb. 18, 2025

(54) CROSSLINKER COMPRISING GENIPIN FOR USE IN PREPARATION OF SENSING FILM OR DIFFUSION CONTROL FILM OF ELECTROCHEMICAL SENSOR

(71) Applicant: I-SENS, INC., Seoul (KR)

(72) Inventors: In Seok Jeong, Seoul (KR); Hyunhee Yang, Seoul (KR); Young Jea Kang, Seoul (KR)

(73) Assignee: I-SENS, INC., Seoul (KR)

( * ) Notice: Subject to any disclaimer, the term of this patent is extended or adjusted under 35 U.S.C. 154(b) by 928 days.

(21) Appl. No.: 16/972,540

(22) PCT Filed: May 9, 2019

(86) PCT No.: PCT/KR2019/006001
§ 371 (c)(1),
(2) Date: Nov. 3, 2021

(87) PCT Pub. No.: WO2019/235755
PCT Pub. Date: Dec. 12, 2019

(65) Prior Publication Data
US 2022/0057355 A1 Feb. 24, 2022

(30) Foreign Application Priority Data
Jun. 8, 2018 (KR) .......... 10-2018-0066188

(51) Int. Cl.
*G01N 27/327* (2006.01)
*C07D 311/94* (2006.01)
(Continued)

(52) U.S. Cl.
CPC ....... *G01N 27/3277* (2013.01); *C07D 311/94* (2013.01); *C08K 5/1545* (2013.01); *C12Q 1/005* (2013.01); *G01N 27/3271* (2013.01)

(58) Field of Classification Search
CPC .......... G01N 27/3277; G01N 27/3271; G01N 27/3272; G01N 27/3335; G01N 27/302;
(Continued)

(56) References Cited

U.S. PATENT DOCUMENTS 4,581,336 A * 4/1986 Malloy .................. C12Q 1/003
204/403.14
5,120,420 A * 6/1992 Nankai .................. C12Q 1/004
435/817
(Continued)

FOREIGN PATENT DOCUMENTS

JP 07016409 B2 6/1988
JP 2009528083 A 8/2009
(Continued)

OTHER PUBLICATIONS

Ichi et al., "Bioelectrodes modified with chitosan for long-term energy supply from the body," Energy Environ. Sci. 2015, 8, 1017 (Year: 2015).*
(Continued)

Primary Examiner — Alexander S Noguerola
(74) Attorney, Agent, or Firm — Polsinelli PC

(57) ABSTRACT

The present disclosure relates to a composition for a crosslinking agent for the preparation of a sensing layer or a diffusion control layer of an electrochemical biosensor comprising genipin or a derivative thereof, in which due to the properties of genipin that can be extracted and used from plants, not only it has high biocompatibility compared to conventional crosslinking agents with high toxicity, but also it can easily confirm the progress of the reaction by measuring UV or measuring the amount of amine groups present when reacting with a compound having an amine group, for example, an electron transport medium, and additionally, it has the advantage of suppressing a rapid decrease in sensor
(Continued)

life due to high concentration of glucose while maintaining an appropriate sensitivity to glucose.

17 Claims, 5 Drawing Sheets

(51) Int. Cl.
 *C08K 5/1545* (2006.01)
 *C12Q 1/00* (2006.01)
(58) Field of Classification Search
 CPC .... G01N 27/40; C07D 311/94; C08K 5/1545; C12Q 1/005; C12Q 1/002
 See application file for complete search history.

(56) References Cited

U.S. PATENT DOCUMENTS

| | | | |
|---|---|---|---|
| 8,663,686 B2 | 3/2014 | Zhang et al. | |
| 2008/0029390 A1* | 2/2008 | Roche | A61B 5/14532 435/14 |
| 2010/0203144 A1 | 8/2010 | Laurencin et al. | |
| 2015/0080691 A1* | 3/2015 | Boock | A61B 5/14865 600/347 |
| 2017/0350850 A1 | 12/2017 | Yoon et al. | |

FOREIGN PATENT DOCUMENTS

| | | | |
|---|---|---|---|
| JP | 2009264920 A | 11/2009 |
| JP | 2015534483 A | 12/2015 |
| KR | 1020130084377 A | 7/2013 |
| KR | 101512566 B1 | 4/2015 |
| KR | 1020160082160 A | 7/2016 |
| KR | 1020160107464 A | 9/2016 |

OTHER PUBLICATIONS

Fernandes et al., "Genipin-Cross-Linked Chitosan as a Support for Lacase Biosensor," Electroanalysis 2013, 25, No. 2, 557-566 (Year: 2013).*
Ahmed et al., "Genipin, a natural blue colorant precursor: Source, extraction, properties, and applications," Food Chemistry 434 (2024) 137498 (Year: 2024).*
Mot et al., "Laccases: Complex Architectures for One-Electron Oxidations," ISSN 0006_2979, Biochemistry (Moscow), 2012, vol. 77 , No. 12, pp. 1395-1407. @ Pleiades Publishing, Ltd., 2012. (Year: 2012).*
Brenda Information on EC 1.10.3.2—laccase, released Jan. 2023(Jan. 2023), https://www.brenda-enzymes.org/enzyme.php?ecno=1.10.3.2 (Year: 2023).*
Arslan et al., A New Laccase-Based Biosensor for Epinephrine Determination, Gazi University Journal of Science GU J Sci 28(1):1-9 (2015) (Year: 2015).*
Li et al.,"A disposable biosensor based on immobilization of laccase with silica spheres on the MWCNTs-doped screen-printed electrode," Chemistry Central Journal 2012, 6:103 (Year: 2012).*
KIPO (Korean Intellectual Patent Office) machine-generated English language translation of KR 10-2016-0107, patent published 20220721 (Year: 2022).*
English abstract for JP2009264920; retrieved from www.espacenet.com on Nov. 4, 2021.
International Search Report and Written Opinion for PCT/KR2019/006001 mailed on Aug. 20, 2019.
Translation of International Search Report for PCT/KR2019/006001 mailed on Aug. 20, 2019.
Peng, Chiung-Huei, et al., "Penta-Acetyl Geniposide Induce Apoptosis in C6 Glioma Cells by Modulating the Activation of Neutral Sphingomyelinase-Induced p75 Nerve Growth Factor Receptor and Protein Kinase Cō Pathway", Molecular Pharmacology, 70(3), 997-1004, 2006.
Chiba, Kenzo, et al., "Neuritogenesis of Herbal Geniposide-Related Compounds in PC12h Cells", Journal of Health Science, 52(6), 743-747, 2006.
Fernandes, S. C, et al., "Genipin-Cross-Linked Chitosan as a Support for Laccase Biosensor" Electroanalysis, 2013, vol. 25, No. 2, pp. 557-566 (Jan. 24, 2013).
English Translation of KR1020160107464 from www.engpat.kipris.or.kr.
English Translation of KR101512566 from www.espacenet.com.
English Translation of KR1020160082160 from www.espacenet.com.
English Translation of KR1020130084377 from www.engpat.kipris.or.kr.
Office Action for EP Application No. 19814903.1, mailed Jun. 11, 2024, 4 pages.

* cited by examiner

[FIG. 1]
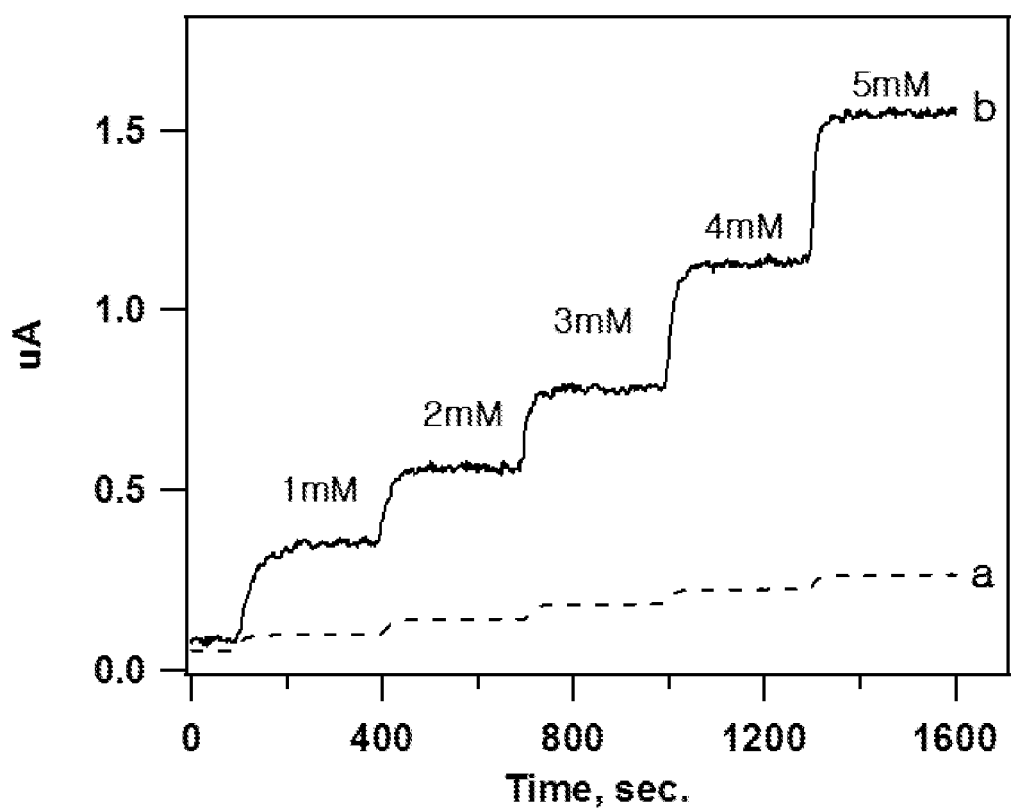

[FIG. 2]
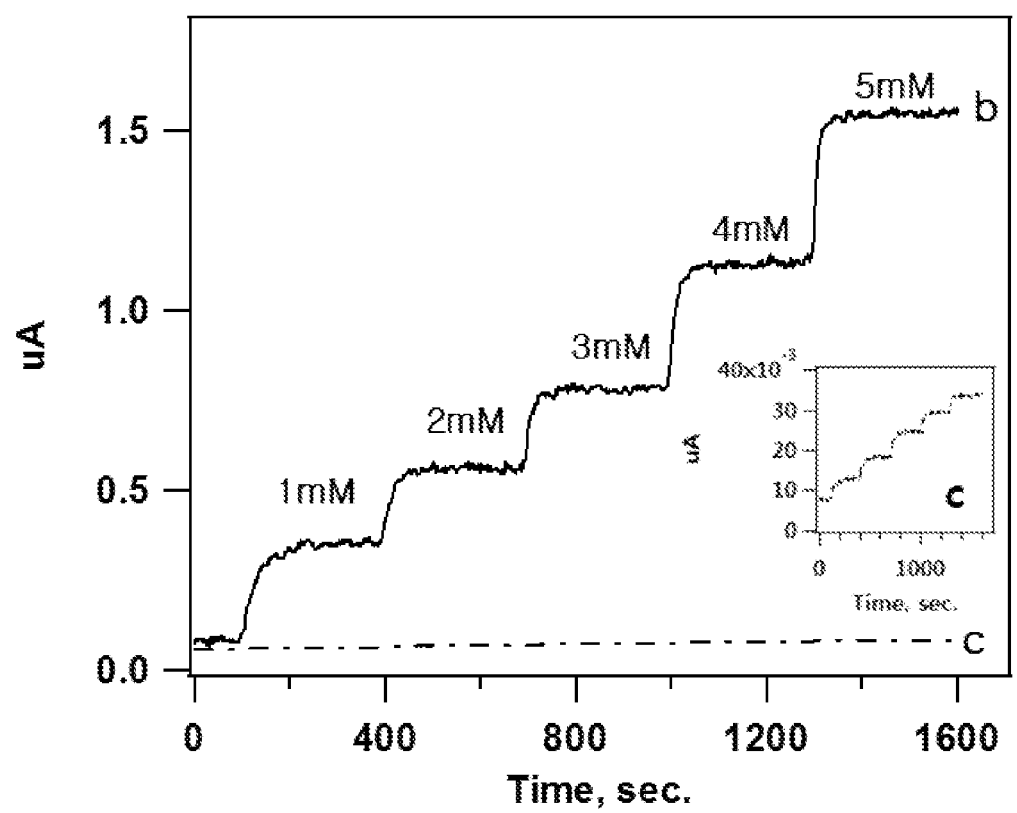

[FIG. 3]
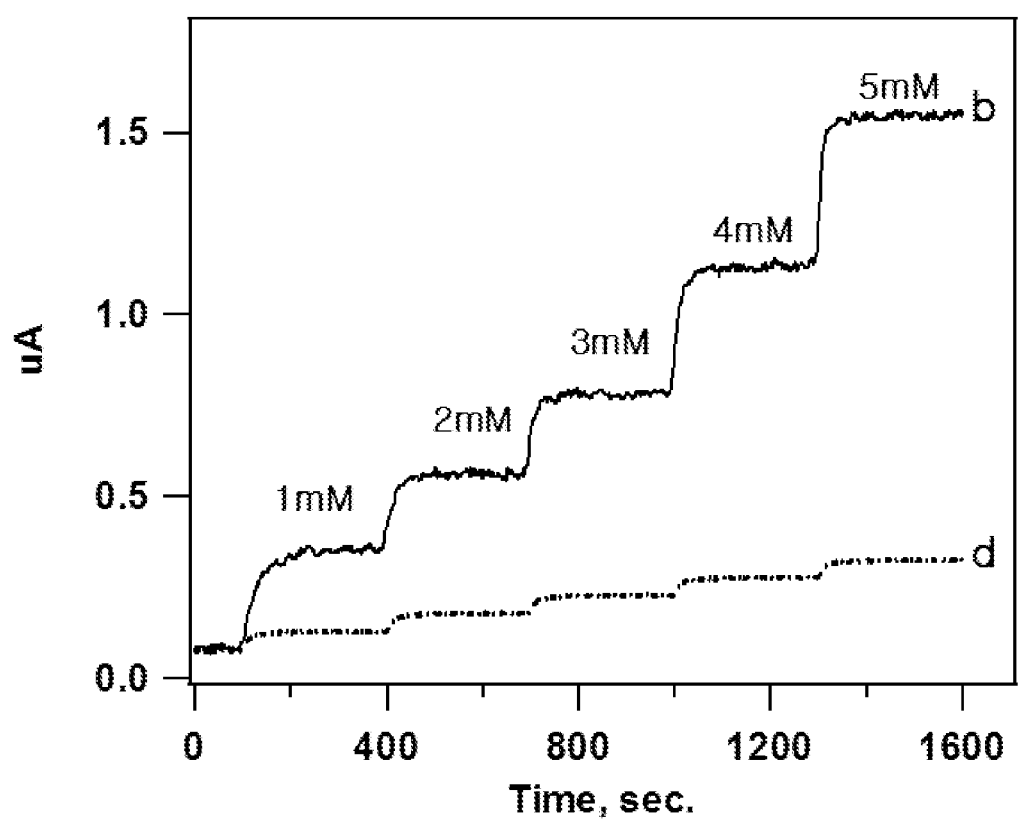

[FIG. 4]
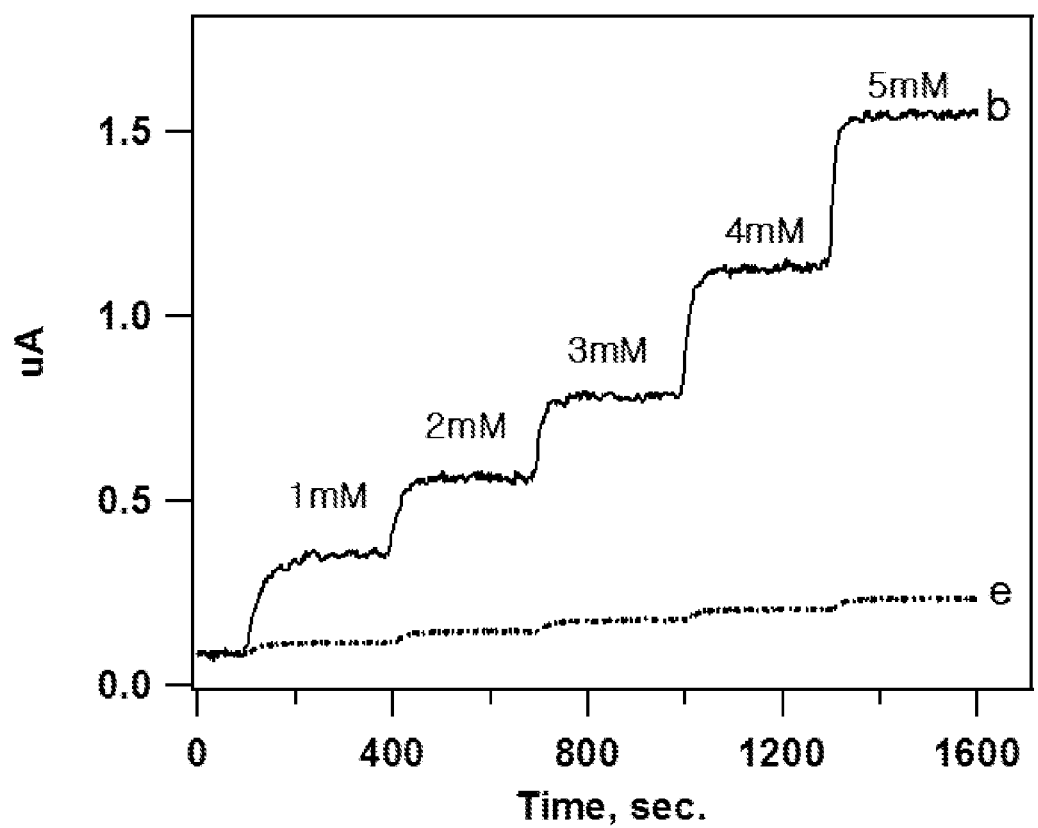

[FIG. 5]
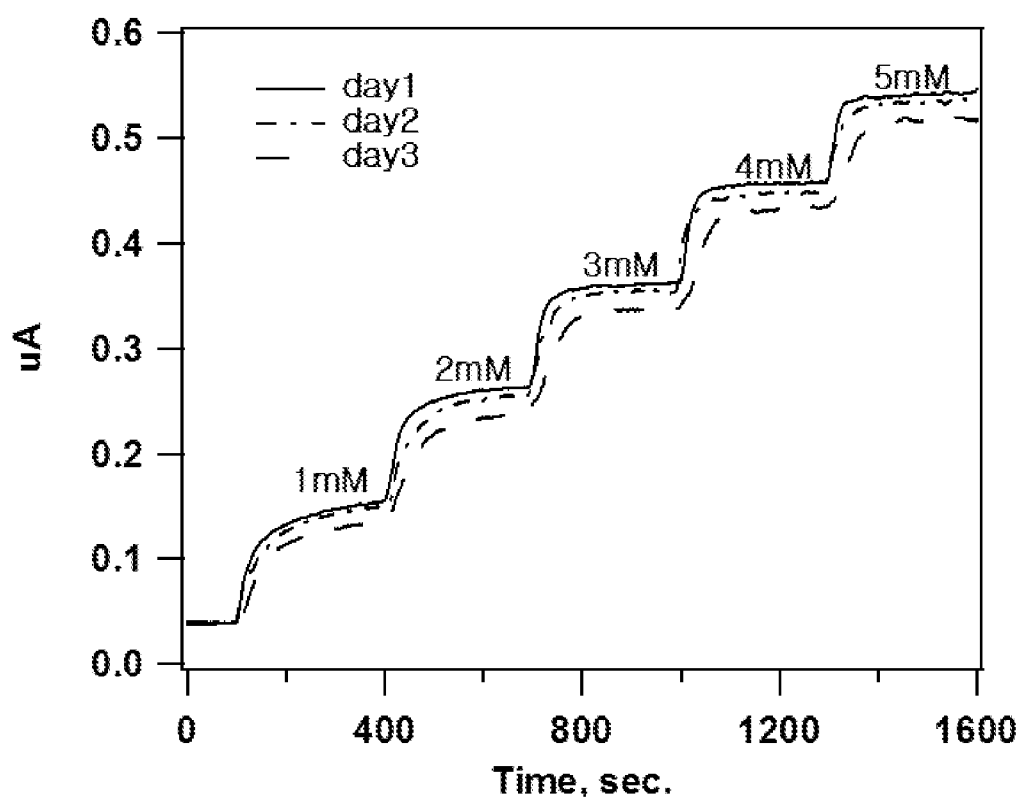

CROSSLINKER COMPRISING GENIPIN FOR USE IN PREPARATION OF SENSING FILM OR DIFFUSION CONTROL FILM OF ELECTROCHEMICAL SENSOR

TECHNICAL FIELD

Cross-Reference to Related Application(s)

This application claims the benefit of Korean Patent Application No. 10-2018-0066188 filed on Jun. 8, 2018 with the Korean Intellectual Property Office, the disclosure of which is incorporated herein by reference in its entirety.

The present disclosure relates to a novel crosslinking agent used in the preparation of an electrochemical sensor, and more particularly to a novel use of genipin as a crosslinking agent used in the preparation of a sensing layer or a diffusion control layer in an electrochemical sensor for blood glucose measurement.

BACKGROUND ART

Recently, interest in the development of biosensors is increasing day by day for quantitative and qualitative analysis of target analytes from the medical field to the environment and food fields. In particular, an enzymatic biosensor is a chemical sensor used to selectively detect and measure chemical substances contained in a sample by utilizing the biological detection function in which a functional substance of an organism or an organism such as a microorganism reacts sensitively with a specific substance, and it has been mainly developed for medical applications such as blood glucose sensors, and is also being studied even in applications in the fields of food engineering and environmental measurement.

Periodic measurement of blood glucose is very important in the management of diabetes. Therefore, various blood glucose level measuring devices are being developed including a portable measuring device that easily measure blood glucose levels. The operating principle of such a biosensor is based on an optical method or an electrochemical method. Such an electrochemical biosensor can reduce the influence of oxygen, unlike a biosensor using a conventional optical method, and has the advantage that it can be used without any separate pretreatment even if the sample becomes turbid. Therefore, various types of electrochemical biosensors with accuracy and precision are widely used.

Currently commercialized electrochemical blood glucose sensors mainly use enzyme electrodes. More specifically, it has a structure in which a glucose oxidase is immobilized on an electrode capable of converting an electrical signal by a chemical or physical method. These electrochemical blood glucose sensors are based on the principle of measuring the electric current generated by transferring electrons generated by the enzymatic oxidation of glucose in analytes such as blood to the electrodes, thereby providing the glucose concentration in the analyte. In order to stably immobilize these enzymes, a polymeric support is required, and a crosslinking agent such as glutaraldehyde or ethylene glycol-diglycidylether must be used to prepare such a polymeric support. In addition, such a crosslinking agent may be used in the preparation of a diffusion control layer used to regulate or limit the amount of glucose flowing in from a biological sample.

Furthermore, in the case of using such a biosensor, the ability to obtain accurate and rapid measurement values with a small amount of sample volume is very important to maximize user convenience. Therefore, the development of a new electron-transport medium capable of achieving the shorter measurement time than the conventional electron-transport medium is required.

On the other hand, a continuous glucose monitoring (CGM) system is used to continuously monitor blood glucose levels and manage diseases such as diabetes. However, existing enzymatic glucose can induce considerable pain due to the conventional finger-pricking method with a needle during a blood collection, which may reduce patient compliance, therefore may not be used as a CGM. In order to solve such problem, an improved version of a continuous glucose monitoring sensor (CGMS) that can adhere to the body and minimal invasiveness has recently been developed. In the case of an subcutaneously-invasive enzymatic CGMS sensor, an electron-transfer mediator containing a transition metal, may be included in a part entering the body, a polymer support that fixes the electron transfer mediator, a crosslinking agent or the like that is used in the preparation of the diffusion control layer, and which may be included in the sensor is absorbed by the human body to cause toxicity and side effects. The use and development of safe technologies or substances capable of minimizing such problems is widely in demand.

DETAILED DESCRIPTION OF THE INVENTION

Technical Problem

It is one object of the present disclosure to provide a novel crosslinking agent used in the preparation of a sensor material that enables quantitative and qualitative analysis of blood glucose levels, specifically, a polymeric support of a sensing layer that performs the role in assisting enzyme stabilization and dispersion in electrochemical sensors, or in the preparation of a diffusion control layer.

Technical Solution

In order to achieve the above object, the present disclosure provides a crosslinking agent containing genipin, which is used in the preparation of a polymeric support of a sensing layer or the preparation of a diffusion control layer in electrochemical sensors, a sensing layer or diffusion control layer prepared using the same, and an electrochemical sensor including the sensing layer or the diffusion control layer.

Advantageous Effects

When a polymeric support of a sensing layer for an electrochemical sensor or a diffusion control layer is prepared by using a crosslinking agent containing genipin according to the present disclosure, it is very useful in the preparation of electrochemical sensors in that due to the properties of genipin that can be extracted and used from plants, not only it has high biocompatibility compared to conventional crosslinking agents with high toxicity, but also it can easily confirm the progress of the reaction by measuring UV or measuring the amount of amine groups present when reacting with a compound having an amine group, for example, an electron transport medium, and additionally, it is very useful in that it exhibits the sensitivity to glucose suitable as a sensor and at the same time, has the advantage of reducing the life of the sensor due to high concentration of glucose.

BRIEF DESCRIPTION OF THE DRAWINGS

FIG. 1 is a graph comparing the changes in glucose sensitivity by the presence or absence of a crosslinking agent containing genipin according to the present disclosure in the preparation of a sensing layer. In FIG. 1, a is the result of an electrode a including a sensing layer without a crosslinking agent, and electrode b corresponds to the result of electrode b including a sensing layer prepared by using genipin as a crosslinking agent.

FIG. 2 is a graph comparing the changes in glucose sensitivity according to the present or absence of the introduction of a PVI diffusion control layer prepared by using a crosslinking agent containing genipin according to the present disclosure. In FIG. 2, b is the result of an electrode b having a sensing layer prepared by using genipin as a crosslinking agent but not having a diffusion control layer, and c shows the result of an electrode c having a sensing layer prepared by using genipin as a crosslinking agent and a PVI diffusion control layer prepared by using genipin as a diffusion control layer.

FIG. 3 is a graph comparing the changes in glucose sensitivity according to the presence or absence of the introduction of a gelatin diffusion control layer prepared by using a crosslinking agent containing genipin according to the present disclosure. In FIG. 3, b is the result of an electrode b having a sensing layer prepared by using genipin as a crosslinking agent but not having a diffusion control layer, and d shows the result of an electrode d having a sensing layer prepared by using genipin as a crosslinking agent and having a gelatin diffusion control layer prepared by using genipin as a diffusion control layer.

FIG. 4 is a graph comparing the changes in glucose sensitivity according to the presence or absence of the introduction of a chitosan diffusion control layer prepared by using a crosslinking agent containing genipin according to the present disclosure. In FIG. 4, b is the result of an electrode b having a sensing layer prepared by using genipin as a crosslinking agent but not having a diffusion control layer, e shows the result of an electrode d having a sensing layer prepared by using genipin as a crosslinking agent and having a chitosan diffusion control layer prepared by using genipin as a crosslinking agent as a diffusion control layer.

FIG. 5 is a graph confirming the glucose sensitivity during long-term storage in a high concentration of glucose of an electrode d using genipin as a crosslinking agent according to the present disclosure.

DETAILED DESCRIPTION OF THE EMBODIMENTS

Hereinafter, the present disclosure will be described in detail.

As one aspect for achieving the above object, the present disclosure relates to a composition for a crosslinking agent for preparing a sensing layer or a diffusion control layer for an electrochemical biosensor containing genipin or a derivative thereof, or the use of genipin as an electrochemical biosensor crosslinking agent.

As used herein, the term "genipin" refers to a component showing the main pharmacological efficacy of gardenia fruit (gardenum) as a non-sugar part of geniposide which is a natural component of iridoid glycosides, and can be represented by the following Chemical Formula 1. Genipin has been reported have other pharmacological uses, such as promoting the secretion of gastric acid, inhibiting antioxidant activity, inhibitory activity of nitric oxide (NO) production or pathological tissue lesions in a liver toxicity model, but the use of the electrochemical biosensor clarified in the present disclosure, particularly a crosslinking agent for crosslinking polymeric monomers in the preparation of a sensing layer or diffusion control layer used in a biosensor, has been investigated for the first time by the present inventors.

[Chemical Formula 1]

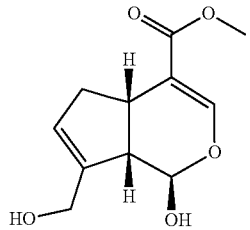

The term "derivative of genipin" as used herein exhibits the same activity as genipin, and includes compounds having crosslinking use for polymeric monomers without limitation. For example, geniposide, genipiodisic acid, pentaacetyl geniposide (Molecular Pharmacology, 70(3), 997-1004, 2006), 6a-hydroxygeniposide, 6b-hydroxygeniposide, 6a-methoxygeniposide, 6b-methoxygeniposide (Journal of Health Science, 52(6), 743-747, 2006) or the like may be mentioned, without being limited thereto.

In the present disclosure, the genipin is reduced by reacting with a metabolite to be measured by an electrochemical sensor, and constitutes a sensing layer with an enzyme that catalyzes a redox reaction in a living organism, and can be used as a crosslinking agent for immobilizing on a water-soluble polymeric support that perform a role in assisting stabilization and dispersion of enzymes. Such a polymeric support may also be connected to an electron transport medium contained in the sensing layer. In this case, a material including an amine group ($NH_2$) at the end of the electron transport medium or the electron transport medium complex can be used to easily perform crosslinking with the genipin.

Further, the genipin may be used as a crosslinking agent in the preparation of a water-soluble polymer diffusion control layer in an electrochemical sensor.

In conventional electrochemical sensors, the crosslinking agents used for the polymeric support in the sensing layer or diffusion control layer as described above include highly toxic substances such as glutalaldehyde, ethylene glycoldiglycidylether, and the like. However, in the case of using these crosslinking agents, if there exists a part that is inserted into a certain part of the human body, like an electrochemical sensor, particularly a continuous blood glucose measurement sensor, it is highly likely to have an adverse effect on the human body due to its own toxicity. However, genipin, which is the crosslinking agent according to the present disclosure, is a material that can be extracted from plants and used, and has the advantage of being very useful in the preparation of an electrochemical sensor in that it has a high biocompatibility compared to conventional highly toxic crosslinking agents. Furthermore, it has the advantage that the progress of the reaction can be easily confirmed by measuring UV or measuring the amount of amine groups present when reacting a compound having an amine group, for example, an electron transport medium, As a polymer that can be used as a crosslinking agent of the genipin according to the present disclosure, polymers having heterocycles having N atoms such as polyvinyl pyrrolidone (PVP) and polyvinyl imidazole, polyvinyl alcohol (PVA), polyfluorosulfonate (perfluoro sulfonate), hydroxyethyl cellulose (HEC), hydroxypropyl cellulose (HPC), carboxy methyl cellulose (CMC), cellulose acetate, polyamide, chitosan, gelatin, and the like can be mentioned, without being limited thereto. The genipin according to the present disclosure may be used at a level sufficient for crosslinking the polymer.

In another aspect, the present disclosure relates to a sensing layer for an electrochemical sensor prepared by using the genipin as a crosslinking agent. The sensing layer may include an electron transport medium and an oxidoreductase in addition to a polymeric support prepared by including genipin as a crosslinking agent.

Oxidoreductase is a generic term for an enzyme that catalyzes the redox reaction in a living organism. In the case of a target substance to be measured in the present disclosure, such as a biosensor, it refers to an enzyme that is reduced by reacting with a metabolite to be measured. The enzyme reduced in this way reacts with the electron transport medium. At this time, the metabolite is quantified by measuring signals such as current change. The oxidoreductase usable in the present disclosure may be at least one selected from the group consisting of various dehydrogenase, oxidase, esterase, and the like. Depending on the redox or detection target material, an enzyme using the target material as a substrate may be selected and used from among enzymes belonging to the enzyme group.

More specifically, the oxidoreductase may be one or more selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, bilirubin oxidase, and the like.

On the other hand, the oxidoreductase can also contain a cofactor that plays a role of storing hydrogen deprived by the oxidoreductase from the target substance (e.g., metabolite) to be measured. For example, one or more selected from the group consisting of flavin adenine dinucleotide (FAD), nicotinamide adenine dinucleotide (NAD), pyrroloquinoline quinone (PQQ) and the like may be mentioned.

Further, the electron transport medium reacts with metabolites and is reduced by redox reaction with the reduced enzyme, and the electron transfer medium in the reduced state formed in this way plays a role of generating an electric current on the electrode surface to which an oxidation potential is applied. The electron transport medium may be one or two or more, and may be a metal-containing complex including one or more selected from the group consisting of Ru, Fe, Os, Rh, Mo, and Ir, without being limited thereto.

In yet another aspect, the present disclosure relates to an electrochemical sensor prepared by using the genipin as a crosslinking agent. The electrochemical sensor may preferably be an electrochemical sensor for measuring blood glucose levels, more preferably, a continuous blood glucose monitoring sensor.

Specifically, the type of the electrochemical biosensor is not limited, but a continuous blood glucose monitoring sensor can be preferably used.

In the configuration of such a continuous blood glucose monitoring sensor, the present disclosure may include, for example, an electrode, an insulator, a substrate, a sensing layer including the electron transfer medium and an oxidoreductase, and a diffusion control layer, a protection layer, and the like. In the case of an electrode, it may include two types of electrodes such as a working electrode and a counter electrode, and it may also include three types of electrodes such as a working electrode, a counter electrode, and a reference electrode. In one embodiment, the biosensor according to the present disclosure may be an electrochemical biosensor prepared by coating a reagent composition containing an electron transfer medium and an enzyme capable of oxidizing and reducing a liquid biological sample, onto a substrate having at least two, preferably two or three electrodes, and then drying it. For example, there is provided a planar electrochemical biosensor, characterized in that in the electrochemical biosensor, an working electrode and a counter electrode are provided on opposite surfaces of a substrate, and a sensing layer cross-linked by using the genipin according to the present disclosure is stacked on the working electrode, and a diffusion control layer and a protective film cross-linked using an insulator and a genipin are sequentially stacked on both sides of a substrate having an working electrode and a counter electrode.

In a specific embodiment, the substrate may be made of one or more materials selected from the group consisting of polyethylene terephthalate (PET), polycarbonate (PC), and polyimide (PI).

Further, as the working electrode, a carbon, gold, platinum, silver or silver/silver chloride electrode may be used.

Further, in the case of an electrochemical biosensor having two electrodes, since the counter electrode plays the role of a reference electrode, gold, platinum, silver or silver/silver chloride electrodes can be used as the counter electrode. In the case of a 3-electrode electrochemical biosensor including up to the reference electrode, a gold, platinum, silver, or silver/silver chloride electrode may be used as the reference electrode, and a carbon electrode may be used as the counter electrode.

As a non-limiting example, in the case of two electrodes, silver chloride or silver may be used because the counter electrode plays the role of the reference electrode, and in the case of three electrodes, silver chloride or silver may be used as the reference electrode, and a carbon electrode may be used as the counter electrode.

In yet another aspect, the present disclosure relates to a method for preparing an electrochemical biosensor, comprising preparing a sensing layer or a diffusion control layer using genipin as a crosslinking agent. The method for preparing the electrochemical biosensor according to the present disclosure is characterized in that genipin is used as a crosslinking agent for the preparation of a sensing layer or a diffusion control layer, and specific preparation processes, reagents, etc. can be used without limitation on the method for preparing the electrochemical biosensor. Preferably, according to the method for preparing the electrochemical biosensor, it is possible to provide a biosensor with increased sensitivity to high concentrations of glucose and increased electrode life.

In a specific embodiment, the present inventors have synthesized osmium-polymer PVI-Os(bpy)$_2$Cl as an electron transport medium by using genipin as a crosslinking agent, and have prepared a sensing layer using the same. Further, they have prepared a diffusion control layer by using genipin as a crosslinking agent to thereby prepare a working electrode. Then, a sensing layer and a diffusion control layer containing an osmium-polymer prepared without using a crosslinking agent are used to prepare a working electrode, and the performance as an electrochemical sensor is confirmed. As a result, when a sensing layer using a crosslinking agent containing genipin is applied to the electrode, it has the effect of effectively forming a sensing layer on the electrode surface and thus increasing the sensitivity. When a diffusion control film using a crosslinking agent containing genipin is applied to an electrode, it can be confirmed that it has the effect of reducing the diffusion of glucose and thus improving the sensitivity and linearity to a high concentration of glucose, and at the same time, shortening the rapid decrease in the life of the electrode due to the damage of the electrode by the high concentration of glucose. Thus, it has been confirmed that genipin can be used as a very useful crosslinking agent in the preparation of electrochemical sensors, particularly in the preparation of sensor layers or diffusion control layers.

Hereinafter, the present disclosure will be described in more detail with reference to examples. However, the following examples are for illustrative purposes only, and the contents of the present disclosure are not limited by the following examples.

EXAMPLE

Reference Example 1: Synthesis of Electron Transport Medium Osmium-Polymer (Os-Polymer)

For the preparation of the sensing layer, an osmium-polymer (PVI-Os (bpy)$_2$Cl$_2$) having the following Chemical Formula 2 was prepared.

[Chemical formula 2]

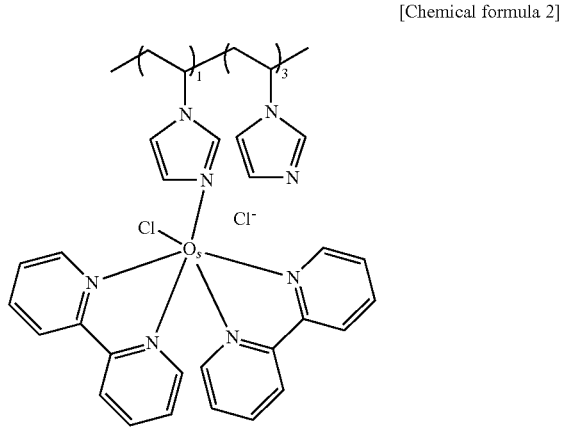

1-1: Synthesis of Os(bpy)$_2$Cl$_2$

For the preparation of PVI-Os(bpy)$_2$Cl$_2$, first, Os(bpy)$_2$Cl$_2$ was synthesized according to the following Reaction Scheme 1.

[Reaction Scheme 1]

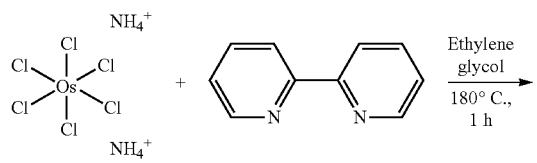

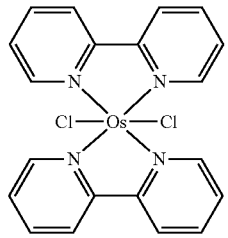

5 g (11.4 mmol) of ammonium hexachloroosmate (IV), 3.56 g (22.8 mmol) of 2,2-bipyridine, and 150 ml of ethylene glycol were added to a 250 ml round bottom flask, and the mixture was stirred for 1 hour while raising the temperature to 180° C. After completion of the reaction, the reaction solution was cooled to room temperature, 20 L of a 1M aqueous solution of sodium hydrosulfite reducing agent was added, and the resulting solid was filtered, washed with distilled water and ethylene ether, and dried to obtain Os(bpy)$_2$Cl$_2$. (1 g/77%) HRMS (Calculated for 574.0367, Found: 574.0362)

1-2: Synthesis of PVI-Os(bpy)$_2$Cl

Using Os(bpy)$_2$Cl$_2$ prepared in Reference Example 1-1, PVI-Os(bpy)$_2$Cl was synthesized according to the following Reaction Scheme 1.

[Reaction Scheme 2]

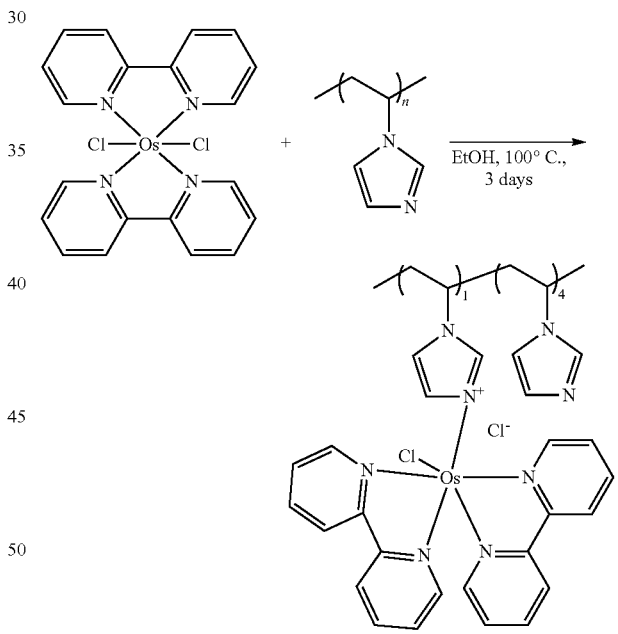

0.82 g (8.7 mmol) of PVI, 1 g (1.74 mmol) of Os(bpy)$_2$Cl$_2$, and 25-30 ml of ethanol were added to a 100 ml round bottom flask, and the mixture was stirred for 3 days while raising the temperature to 100° C. After completion of the reaction, the temperature of the reaction solution was lowered to room temperature, and then the reaction solution was added dropwise to 1 L of an ether solution to form a precipitate. The resulting solid was filtered, washed with ether, and dried to obtain PVI-Os(bpy)$_2$Cl. (1.5 g/82%)

Example 1: Preparation of Sensing Layer

In order to confirm the performance of the crosslinking agent for the preparation of an electrochemical sensor containing genipin according to the present disclosure, a sensing layer using genipin (Sigmaaldrich, product number: g4796) was prepared by the following experimental method based on the composition and weight ratio shown in Table 1 below.

TABLE 1

Weight ratio by composition of sensing layer*

| Electrode name included | Os-polymer | Genipin | Glucose oxidase (GOx) |
|---|---|---|---|
| a | 100 | — | 67.0 |
| b | 100 | 10 | 67.0 |
| c-e | 100 | 10 | 67.0 |

*Relative weight ratio of genipin and glucose oxidase when using 100wt % of Os-polymer ① 10 mg of the Os-polymer prepared in Reference Example 1 was dissolved in 1 mL of 0.1 M acetic acid buffer (pH 5.0) solution.
② 5 mg of genipin was dissolved in 1 mL of a mixed solution of DMSO and deionized water in a ratio of 1:9.
③ 40 mg of glucose oxidase was dissolved in 1 mL of deionized water.
④ 80 uL of genipin solution prepared in step ② were added to 400 uL of Os-polymer solution prepared in step ①, to a certain amount of Os-polymer solution, and reacted for 30 minutes to prepare a reaction solution containing Os-polymer and genipin.
⑤ 67 uL of glucose oxidase solution prepared in step ③ was added to the reaction solution containing Os-polymer and genipin prepared in step ④, and reacted for 10 minutes.
⑥ 5 μL of the solution prepared in step ⑤ was dropped on the carbon printing electrode, and then dried at 23° C. for 24 hours.

Example 2: Preparation of Diffusion Control Layer

Through the following steps, a diffusion control layer for preparing an electrochemical sensor was prepared according to the composition and weight ratio shown in Table 2 below.

TABLE 2

Weight ratio by composition of diffusion control layer*

| Electrode name included | PVI | Gelatin | Chitosan | Genipin |
|---|---|---|---|---|
| c | 100 | — | — | 5 |
| d | — | 100 | — | 1 |
| e | — | — | 100 | 10 |

*Relative weight ratio of genipin when using 100wt % each of PVI, gelatin and chitosan ① 10 mg of polyvinylimidazole (PVI) was dissolved in 1 mL of a 0.1 M acetic acid buffer (pH5.0) solution.
② 10 mg of gelatin was dissolved in 1 mL of 0.1 M acetic acid buffer (pH5.0) solution.
③ 5 mg of chitosan was dissolved in 1 mL of 0.1M acetic acid buffer (pH5.0) solution.
④ 5 mg of genipin was dissolved in 1 mL of a mixed solution of DMSO and deionized water in a ratio of 1:9.
⑤ PVI solution and the genipin solution prepared in step ④, the gelatin solution and genipin solution prepared in step ②, and the chitosan solution prepared in step ③ and the genipin solution prepared in step ④ were mixed according to the weight ratio shown in Table 2, and reacted for 1 hour.
⑥ 10 μL was dropped on the sensing layer and dried at 23° C. for 24 hours to prepare a diffusion control layer.

Example 3: Preparation of Working Electrode

A working electrode was prepared by using the sensing layer and the diffusion control layer prepared in Examples 1 and 2.

A screen-printed carbon electrode (diameter: 5 mm) was used. In the case of electrodes a and b, each of the sensing layers prepared in Example 1 were placed on the carbon electrode and dried to prepare a working electrode. Further, in the case of electrodes c, d and e, each of the sensing layers prepared in Example 1 was placed on the carbon electrode, dried, and then each of the diffusion control layers prepared in Example 2 was stacked on the sensing layer and dried to prepare a working electrode.

Experimental Example 1: Confirmation of the Performance of the Electrochemical Sensor In order to confirm the performance of the electrochemical sensor including the crosslinking agent containing genipin according to the present disclosure, the change in the electrical signal according to the glucose concentration was measured by the following experimental conditions and methods.

Experimental Materials/Conditions

Working electrode: electrodes a, b, c, d and e prepared in Example 3
Reference electrode: Ag/AgCl electrode
Counter electrode: Platinum rod
Test parameters
Equipment: CHI instrument
Technique: amperometric i-t curve
Applied potential: 0.35V
Background electrolyte: 10 mM PBS, pH7.4 (140 mM NaCl)

Experiment Method 50 mL of a PBS solution was added to a beaker, and the electrode containing the sensing layer and/or the diffusion control layer prepared in Examples 1 and 2 were immersed therein, and then stabilized for 30 minutes. When the stabilization was complete, a high concentration of glucose solution was added to a beaker containing the PBS buffer (10 mM PBS, pH 7.4 (140 mM NaCl)), and the electrode was immersed therein, and the change in signal according to the concentration was measured. The concentration of glucose was set to 1 mM, 2 mM, 3 mM, 4 mM and 5 Mm, respectively. The experimental results are shown in FIGS. 1 to 4 and Table 3, respectively.

TABLE 3

| | Glucose sensitivity slope | | | | |
|---|---|---|---|---|---|
| Category | a | b | c | d | e |
| Slope | 0.041 | 0.297 | 0.005 | 0.049 | 0.030 |
| Intercept | 0.016 | −0.012 | 0.008 | 0.080 | 0.086 |

As can be seen in Table 3 and FIG. 1, when the electrode a including the sensing layer not containing the crosslinking agent according to the present disclosure and the electrode b including the sensing layer prepared by using the crosslinking agent containing genipin were immersed in a buffer solution containing glucose, respectively, it was confirmed that the electrode a prepared without a crosslinking agent continuously eluted from the electrode surface.

Also, comparing the sensitivities, it was possible to obtain the result that the sensitivity of the sensing layer prepared using the crosslinking agent was improved by 7.1 times compared to the sensing layer prepared without using the crosslinking agent.

According to these results, when the cross-linking agent containing genipin according to the present disclosure was used, it was indirectly confirmed that the sensing layer was more effectively formed on the electrode surface than when the crosslinking agent was not used.

Further, as can be seen in Table 3 and FIG. 2, as a result of comparing the changes in glucose sensitivity when PVI was introduced as a diffusion control layer, it was confirmed that the electrode c, which had a diffusion control layer prepared by crosslinking the crosslinking agent genipin and PVI in order to reduce the degree of glucose diffusion, exhibited the effect of lowering the sensitivity to about 1/50 compared to the electrode b having no diffusion control layer.

Further, as can be seen in Table 3 and FIG. 3, as a result of comparing the changes in glucose sensitivity when gelatin was introduced into the diffusion control layer, it was confirmed that the sensor d, which had a diffusion control layer prepared by crosslinking the crosslinking agent genipin and gelatin in order to reduce the degree of glucose diffusion, exhibited the effect of lowering the sensitivity to about 1/6 compared to the electrode b having no diffusion control layer.

Further, as can be seen in Table 3 and FIG. 4, as a result of comparing the changes in glucose sensitivity when chitosan was introduced into the diffusion control layer, it was confirmed that the sensor e, which had a diffusion control layer prepared by crosslinking the crosslinking agent genipin and chitosan in order to reduce the degree of glucose diffusion, exhibited the effect of lowering the sensitivity to about 1/10 compared to the electrode b having no diffusion control layer.

Putting these results together, it was confirmed that when a sensing layer using a crosslinking agent containing genipin was applied to an electrode, it exhibited the effect of effectively forming a sensing layer on the electrode surface and thus increasing the sensitivity, and that when a diffusion control layer using a crosslinking agent containing genipin was applied to an electrode, it exhibited the effect of reducing the diffusion of glucose and thus improving the sensitivity and linearity to a high concentration of glucose, and at the same time, shortening the rapid decrease in the life of the electrode due to the damage of the electrode by the high concentration of glucose.

Experimental Example 2: Confirmation of Sensor Performance Over Time

The performance of the sensor over time was confirmed by using the electrode d prepared according to Example 3. On the 1st day, the electrical signal of the sensor according to the glucose concentration (1 mM, 2 mM, 3 mM, 4 mM and 5 Mm) was measured by the same method as in Experimental Example 1, and subsequently, the sensor was immersed in a PBS buffer solution containing a high concentration of glucose (5 mM), and then stored for 3 days while applying 0.35V at an applied potential.

On the 2n and 3rd days of storage, using the electrodes stored in the high concentration of glucose, the sensitivity of the sensor according to the concentration was confirmed as in the 1st day, and the results are shown in FIG. 5.

As can be seen in FIG. 5, it was confirmed that the slopes of the 2nd and 3rd days were maintained up to 98.8% based on the sensitivity slope of the sensor of the 1st day. This has been found to be very useful in the preparation of electrochemical sensors in that when a sensing layer or a diffusion control layer was prepared by using the crosslinking agent containing jenipin according to the present disclosure and applied to an electrode, it exhibits the sensitivity to glucose suitable as a sensor and at the same time, has the advantage of reducing the life of the sensor due to high concentration of glucose.

The invention claimed is:

1. A sensing layer of an electrochemical sensor, comprising:
   (i) a crosslinking agent for preparation of an electrochemical sensor comprising genipin represented by the following Chemical Formula 1, and
   (ii) a polymer having N atoms selected from the group consisting of polyvinyl pyrrolidone (PVP) and polyvinyl imidazole:

[Chemical Formula 1]

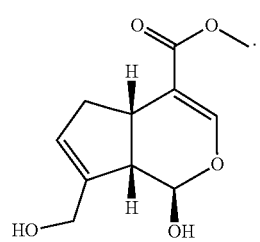

2. The sensing layer of an electrochemical sensor according to claim 1, further comprising an electron transport medium or an oxidoreductase.

3. The sensing layer of an electrochemical sensor according to claim 2, wherein the oxidoreductase is one or more selected from the group consisting of dehydrogenase, oxidase, and esterase.

4. The sensing layer of an electrochemical sensor according to claim 2, comprising, together with the oxidoreductase, one or more cofactors selected from the group consisting of flavin adenine dinucleotide (FAD), nicotinamide adenine dinucleotide (NAD), and pyrroloquinoline quinone (PQQ).

5. A method for preparing an electrochemical biosensor, comprising preparing the sensing layer according to claim 1 using genipin as a crosslinking agent.

6. The method according to claim 5, wherein use of genipin of the following Chemical Formula 1 as a crosslinking agent for the preparation of an electrochemical sensor:

[Chemical Formula 1]

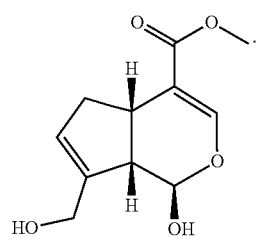

7. An electrochemical sensor, comprising the sensing layer according to claim 1.

8. The electrochemical biosensor according to claim 7, further comprising two or more electrode, an insulator and a substrate.

9. The electrochemical sensor according to claim 7, wherein the sensor is for measuring blood glucose levels.

10. The electrochemical sensor according to claim 9, wherein the sensor is a continuous blood glucose monitoring sensor.

11. A diffusion control layer of an electrochemical sensor comprising:
   (i) a crosslinking agent for the preparation of an electrochemical sensor, comprising genipin represented by the following Chemical Formula 1, and
   (ii) a polymer having N atoms selected from the group consisting of polyvinyl pyrrolidone (PVP) and polyvinyl imidazole:

[Chemical Formula 1]

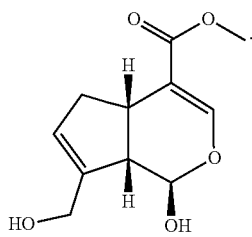

12. An electrochemical sensor, comprising the diffusion control layer according to claim 11.

13. The electrochemical biosensor according to claim 12, further comprising two or more electrode, an insulator and a substrate.

14. The electrochemical sensor according to claim 12, wherein the sensor is for measuring blood glucose levels.

15. The electrochemical sensor according to claim 14, wherein the sensor is a continuous blood glucose monitoring sensor.

16. A method for preparing an electrochemical biosensor, comprising preparing a diffusion control layer according to claim 11 using genipin as a crosslinking agent.

17. The method according to claim 16, wherein use of genipin of the following Chemical Formula 1 as a crosslinking agent for the preparation of an electrochemical sensor:

[Chemical Formula 1]

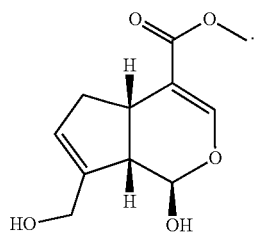

* * * * *